United States Patent
Baril et al.

(10) Patent No.: US 11,839,405 B2
(45) Date of Patent: Dec. 12, 2023

(54) SURGICAL ACCESS DEVICE WITH FIXATION MECHANISM

(71) Applicant: Covidien LP, Mansfield, MA (US)

(72) Inventors: Jacob C. Baril, Norwalk, CT (US); Kevin Desjardin, Prospect, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/963,598

(22) Filed: Oct. 11, 2022

(65) Prior Publication Data

US 2023/0033503 A1 Feb. 2, 2023

Related U.S. Application Data

(62) Division of application No. 16/745,722, filed on Jan. 17, 2020, now Pat. No. 11,464,540.

(51) Int. Cl.
*A61B 17/34* (2006.01)

(52) U.S. Cl.
CPC .. *A61B 17/3423* (2013.01); *A61B 2017/3488* (2013.01)

(58) Field of Classification Search
CPC .......................... A61B 17/3421; A61B 17/3423
See application file for complete search history.

(56) References Cited

U.S. PATENT DOCUMENTS

| | | |
|---|---|---|
| 3,402,710 A | 9/1968 | Paleschuck |
| 3,495,586 A | 2/1970 | Regenbogen |
| 4,016,884 A | 4/1977 | Kwan-Gett |
| 4,112,932 A | 9/1978 | Chiulli |
| 4,183,357 A | 1/1980 | Bentley et al. |
| 4,356,826 A | 11/1982 | Kubota |
| 4,402,683 A | 9/1983 | Kopman |
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |

(Continued)

FOREIGN PATENT DOCUMENTS

| | | |
|---|---|---|
| CA | 2702419 A1 | 11/2010 |
| EP | 0226026 A2 | 6/1987 |

(Continued)

*Primary Examiner* — Si Ming Ku
(74) *Attorney, Agent, or Firm* — Carter, DeLuca & Farrell LLP

(57) ABSTRACT

A surgical access device including a cannula body and a fixation mechanism is disclosed. The cannula body includes a housing, and an elongated portion extending distally from the housing and defining a longitudinal axis. The fixation mechanism includes a sleeve and a spring. The sleeve radially surrounds a portion of the elongated portion of the cannula body. The sleeve is rotatable about the longitudinal axis relative to the elongated portion of the cannula body, and the sleeve is longitudinally translatable relative to the elongated portion of the cannula body. A first portion of the spring is engaged with the sleeve, and a second portion of the spring engaged with a distal portion of the elongated portion of the cannula body. Rotation of the sleeve about the longitudinal axis relative to the elongated portion of the cannula body causes a portion of the spring to move away from the longitudinal axis.

20 Claims, 5 Drawing Sheets

(56) References Cited

U.S. PATENT DOCUMENTS

| | | | |
|---|---|---|---|
| 5,002,557 | A | 3/1991 | Hasson |
| 5,073,169 | A | 12/1991 | Raiken |
| 5,082,005 | A | 1/1992 | Kaldany |
| 5,122,122 | A | 6/1992 | Allgood |
| 5,159,921 | A | 11/1992 | Hoover |
| 5,176,697 | A | 1/1993 | Hasson |
| 5,183,471 | A | 2/1993 | Wilk |
| 5,192,301 | A | 3/1993 | Kamiya et al. |
| 5,209,741 | A | 5/1993 | Spaeth |
| 5,209,754 | A | 5/1993 | Ahluwalia |
| 5,217,466 | A | 6/1993 | Hasson |
| 5,242,409 | A | 9/1993 | Buelna |
| 5,242,415 | A | 9/1993 | Kantrowitz et al. |
| 5,257,973 | A | 11/1993 | Villasuso |
| 5,257,975 | A * | 11/1993 | Foshee .................. A61B 17/34 604/105 |
| 5,269,772 | A | 12/1993 | Wilk |
| 5,290,249 | A | 3/1994 | Foster et al. |
| 5,312,391 | A | 5/1994 | Wilk |
| 5,312,417 | A | 5/1994 | Wilk |
| 5,314,417 | A | 5/1994 | Stephens et al. |
| 5,318,516 | A | 6/1994 | Cosmescu |
| 5,330,486 | A | 7/1994 | Wilk |
| 5,334,143 | A | 8/1994 | Carroll |
| 5,336,169 | A | 8/1994 | Divilio et al. |
| 5,336,203 | A | 8/1994 | Goldhardt et al. |
| 5,337,937 | A | 8/1994 | Remiszewski et al. |
| 5,345,927 | A | 9/1994 | Bonutti |
| 5,360,417 | A | 11/1994 | Gravener et al. |
| 5,366,478 | A | 11/1994 | Brinkerhoff et al. |
| 5,375,588 | A | 12/1994 | Yoon |
| 5,378,588 | A | 1/1995 | Tsuchiya |
| 5,391,156 | A | 2/1995 | Hildwein et al. |
| 5,394,863 | A | 3/1995 | Sanford et al. |
| 5,395,367 | A | 3/1995 | Wilk |
| 5,437,683 | A | 8/1995 | Neumann et al. |
| 5,445,615 | A | 8/1995 | Yoon |
| 5,451,222 | A | 9/1995 | De Maagd et al. |
| 5,460,170 | A | 10/1995 | Hammerslag |
| 5,464,409 | A | 11/1995 | Mohajer |
| 5,480,410 | A | 1/1996 | Cuschieri et al. |
| 5,490,843 | A | 2/1996 | Hildwein et al. |
| 5,507,758 | A | 4/1996 | Thomason et al. |
| 5,511,564 | A | 4/1996 | Wilk |
| 5,514,133 | A | 5/1996 | Golub et al. |
| 5,514,153 | A | 5/1996 | Bonutti |
| 5,520,698 | A | 5/1996 | Koh |
| 5,522,791 | A | 6/1996 | Leyva |
| 5,524,644 | A | 6/1996 | Crook |
| 5,540,648 | A | 7/1996 | Yoon |
| 5,545,150 | A | 8/1996 | Danks et al. |
| 5,545,179 | A | 8/1996 | Williamson, IV |
| 5,556,385 | A | 9/1996 | Andersen |
| 5,569,159 | A | 10/1996 | Anderson et al. |
| 5,577,993 | A | 11/1996 | Zhu et al. |
| 5,601,581 | A | 2/1997 | Fogarty et al. |
| 5,624,399 | A | 4/1997 | Ackerman |
| 5,634,911 | A | 6/1997 | Hermann et al. |
| 5,634,937 | A | 6/1997 | Mollenauer et al. |
| 5,643,285 | A | 7/1997 | Rowden et al. |
| 5,649,550 | A | 7/1997 | Crook |
| 5,651,771 | A | 7/1997 | Tangherlini et al. |
| 5,653,705 | A | 8/1997 | de la Torre et al. |
| 5,656,013 | A | 8/1997 | Yoon |
| 5,672,168 | A | 9/1997 | de la Torre et al. |
| 5,683,378 | A | 11/1997 | Christy |
| 5,685,857 | A | 11/1997 | Negus et al. |
| 5,697,946 | A | 12/1997 | Hopper et al. |
| 5,709,675 | A | 1/1998 | Williams |
| 5,713,858 | A | 2/1998 | Heruth et al. |
| 5,713,869 | A | 2/1998 | Morejon |
| 5,722,962 | A | 3/1998 | Garcia |
| 5,728,103 | A | 3/1998 | Picha et al. |
| 5,730,748 | A | 3/1998 | Fogarty et al. |
| 5,735,791 | A | 4/1998 | Alexander, Jr. et al. |
| 5,741,298 | A | 4/1998 | MacLeod |
| 5,752,970 | A | 5/1998 | Yoon |
| 5,782,817 | A | 7/1998 | Franzel et al. |
| 5,795,290 | A | 8/1998 | Bridges |
| 5,803,921 | A | 9/1998 | Bonadio |
| 5,810,712 | A | 9/1998 | Dunn |
| 5,813,409 | A | 9/1998 | Leahy et al. |
| 5,830,191 | A | 11/1998 | Hildwein et al. |
| 5,836,871 | A | 11/1998 | Wallace et al. |
| 5,836,913 | A | 11/1998 | Orth et al. |
| 5,840,077 | A | 11/1998 | Rowden et al. |
| 5,842,971 | A | 12/1998 | Yoon |
| 5,848,992 | A | 12/1998 | Hart et al. |
| 5,853,417 | A | 12/1998 | Fogarty et al. |
| 5,857,461 | A | 1/1999 | Levitsky et al. |
| 5,865,817 | A | 2/1999 | Moenning et al. |
| 5,871,474 | A | 2/1999 | Hermann et al. |
| 5,876,413 | A | 3/1999 | Fogarty et al. |
| 5,894,843 | A | 4/1999 | Benetti et al. |
| 5,899,208 | A | 5/1999 | Bonadio |
| 5,899,913 | A | 5/1999 | Fogarty et al. |
| 5,904,703 | A | 5/1999 | Gilson |
| 5,906,577 | A | 5/1999 | Beane et al. |
| 5,914,415 | A | 6/1999 | Tago |
| 5,916,198 | A | 6/1999 | Dillow |
| 5,941,898 | A | 8/1999 | Moenning et al. |
| 5,951,588 | A | 9/1999 | Moenning |
| 5,957,913 | A | 9/1999 | de la Torre et al. |
| 5,964,781 | A | 10/1999 | Mollenauer et al. |
| 5,976,174 | A | 11/1999 | Ruiz |
| 5,997,515 | A | 12/1999 | de la Torre et al. |
| 6,017,355 | A | 1/2000 | Hessel et al. |
| 6,018,094 | A | 1/2000 | Fox |
| 6,024,736 | A | 2/2000 | de la Torre et al. |
| 6,030,402 | A | 2/2000 | Thompson et al. |
| 6,033,426 | A | 3/2000 | Kaji |
| 6,033,428 | A | 3/2000 | Sardella |
| 6,042,573 | A | 3/2000 | Lucey |
| 6,048,309 | A | 4/2000 | Flom et al. |
| 6,059,816 | A | 5/2000 | Moenning |
| 6,068,639 | A | 5/2000 | Fogarty et al. |
| 6,077,288 | A | 6/2000 | Shimomura et al. |
| 6,086,603 | A | 7/2000 | Termin et al. |
| 6,099,506 | A | 8/2000 | Macoviak et al. |
| 6,110,154 | A | 8/2000 | Shimomura et al. |
| 6,142,936 | A | 11/2000 | Beane et al. |
| 6,156,006 | A | 12/2000 | Brosens et al. |
| 6,162,196 | A | 12/2000 | Hart et al. |
| 6,171,282 | B1 | 1/2001 | Ragsdale |
| 6,197,002 | B1 | 3/2001 | Peterson |
| 6,217,555 | B1 | 4/2001 | Hart et al. |
| 6,228,063 | B1 | 5/2001 | Aboul-Hosn |
| 6,234,958 | B1 | 5/2001 | Snoke et al. |
| 6,238,373 | B1 | 5/2001 | de la Torre et al. |
| 6,241,768 | B1 | 6/2001 | Agarwal et al. |
| 6,251,119 | B1 | 6/2001 | Addis |
| 6,254,534 | B1 | 7/2001 | Butler et al. |
| 6,264,604 | B1 | 7/2001 | Kieturakis et al. |
| 6,276,661 | B1 | 8/2001 | Laird |
| 6,293,952 | B1 | 9/2001 | Brosens et al. |
| 6,315,770 | B1 | 11/2001 | de la Torre et al. |
| 6,319,246 | B1 | 11/2001 | de la Torre et al. |
| 6,328,720 | B1 | 12/2001 | McNally et al. |
| 6,329,637 | B1 | 12/2001 | Hembree et al. |
| 6,371,968 | B1 | 4/2002 | Kogasaka et al. |
| 6,382,211 | B1 | 5/2002 | Crook |
| 6,423,036 | B1 | 7/2002 | Van Huizen |
| 6,440,061 | B1 | 8/2002 | Wenner et al. |
| 6,440,063 | B1 | 8/2002 | Beane et al. |
| 6,443,957 | B1 | 9/2002 | Addis |
| 6,447,489 | B1 | 9/2002 | Peterson |
| 6,450,983 | B1 | 9/2002 | Rambo |
| 6,454,783 | B1 | 9/2002 | Piskun |
| 6,464,686 | B1 | 10/2002 | O'Hara et al. |
| 6,468,292 | B1 | 10/2002 | Mollenauer et al. |
| 6,485,410 | B1 | 11/2002 | Loy |
| 6,488,620 | B1 | 12/2002 | Segermark et al. |
| 6,488,692 | B1 | 12/2002 | Spence et al. |
| 6,524,283 | B1 | 2/2003 | Hopper et al. |

(56) References Cited

U.S. PATENT DOCUMENTS

| | | |
|---|---|---|
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Wers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Wers et al. |
| 8,109,873 B2 | 2/2012 | Albrecht et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 10,751,086 B2 | 8/2020 | Shipp et al. |
| 11,464,540 B2 | 10/2022 | Baril et al. |
| 2001/0037053 A1 | 11/2001 | Bonadio et al. |
| 2002/0055714 A1 | 5/2002 | Rothschild |
| 2003/0014076 A1 | 1/2003 | Mollenauer et al. |
| 2003/0093104 A1 | 5/2003 | Bonner et al. |

(56) References Cited

U.S. PATENT DOCUMENTS

| | | |
|---|---|---|
| 2003/0187376 A1 | 10/2003 | Rambo |
| 2003/0233115 A1 | 12/2003 | Eversull et al. |
| 2003/0236549 A1 | 12/2003 | Bonadio et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Towell et al. |
| 2005/0277946 A1 | 12/2005 | Greenhalgh |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Ortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0144440 A1 | 6/2011 | Cropper et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0313250 A1 | 12/2011 | Kleyman |
| 2012/0059640 A1 | 3/2012 | Roy et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |

(56) References Cited

U.S. PATENT DOCUMENTS

| | | |
|---|---|---|
| 2013/0310651 A1 | 11/2013 | Alfieri |
| 2014/0018632 A1 | 1/2014 | Kleyman |

FOREIGN PATENT DOCUMENTS

| | | |
|---|---|---|
| EP | 0538060 A1 | 4/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2343019 | 7/2011 |
| GB | 2469083 | 4/2009 |
| WO | 8401512 | 4/1984 |
| WO | 9314801 | 8/1993 |
| WO | 9404067 | 3/1994 |
| WO | 9610963 | 4/1996 |
| WO | 9636283 | 11/1996 |
| WO | 9733520 A1 | 9/1997 |
| WO | 9742889 | 11/1997 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 | 2/2001 |
| WO | 0149363 | 7/2001 |
| WO | 0207611 | 1/2002 |
| WO | 03034908 A2 | 5/2003 |
| WO | 03071926 | 9/2003 |
| WO | 03077726 | 9/2003 |
| WO | 2004043275 | 5/2004 |
| WO | 2004054456 | 7/2004 |
| WO | 2004075741 | 9/2004 |
| WO | 2004075930 | 9/2004 |
| WO | 2005058409 | 6/2005 |
| WO | 2006019723 | 2/2006 |
| WO | 2006100658 A2 | 9/2006 |
| WO | 2006110733 | 10/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 | 6/2008 |
| WO | 2008093313 | 8/2008 |
| WO | 2008103151 | 8/2008 |
| WO | 2008121294 A1 | 10/2008 |
| WO | 2008147644 | 12/2008 |
| WO | 2009036343 | 3/2009 |
| WO | 2010000047 | 1/2010 |
| WO | 2010141409 | 12/2010 |
| WO | 2010141673 | 12/2010 |

\* cited by examiner

SURGICAL ACCESS DEVICE WITH FIXATION MECHANISM

CROSS-REFERENCE TO RELATED APPLICATION

The present application is a Divisional Application of U.S. patent application Ser. No. 16/745,722, filed on Jan. 17, 2020, now U.S. Pat. No. 11,464,540. The entire contents of which is incorporated herein by reference.

BACKGROUND

Technical Field

The present disclosure relates to a surgical access device. More particularly, the present disclosure relates to a surgical access device having a fixation mechanism to help maintain its position relative to a patient during a surgical procedure.

Background of Related Art

In minimally invasive surgical procedures, including endoscopic and laparoscopic surgeries, a surgical access device permits the introduction of a variety of surgical instruments into a body cavity or opening. A surgical access device (e.g., a cannula) is introduced through an opening in tissue (i.e. a naturally occurring orifice or an incision) to provide access to an underlying surgical site in the body. The incision is typically made using an obturator having a blunt or sharp tip that has been inserted within the passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instrumentation through the surgical access device to perform the surgical procedure.

During these procedures, it may be challenging to maintain the position of the surgical access device with respect to the body wall, particularly when exposed to a pressurized environment. To help maintain the position of the surgical access device with respect to the body wall, an expandable anchor or fixation mechanism disposed near a distal end of the surgical access device is occasionally used. Expanding such an anchor while the surgical access device is within the body helps minimize undesired movement of the surgical access device with respect to the body.

Accordingly, it may be helpful to provide a fixation mechanism including a spring to help maintain the longitudinal position of the surgical access device with respect to the patient.

SUMMARY

The present disclosure relates to a surgical access device including a cannula body and a fixation mechanism. The cannula body includes a housing, and an elongated portion extending distally from the housing and defining a longitudinal axis. The fixation mechanism includes a sleeve and a spring. The sleeve radially surrounds a portion of the elongated portion of the cannula body. The sleeve is rotatable about the longitudinal axis relative to the elongated portion of the cannula body and is longitudinally translatable relative to the elongated portion of the cannula body. A first portion of the spring is engaged with the sleeve, and a second portion of the spring engaged with a distal portion of the elongated portion of the cannula body. Rotation of the sleeve about the longitudinal axis relative to the elongated portion of the cannula body causes a portion of the spring to move away from the longitudinal axis. In aspects, the fixation mechanism may include a distal sleeve radially surrounding the distal portion of the fixation sleeve.

In aspects, the fixation mechanism includes a sheath radially surrounding the spring. The sheath may radially surround a distal portion of the sleeve and may radially surround a distal portion of the elongated portion of the cannula body.

In aspects, a proximal portion of the spring is affixed to the sleeve and a distal portion of the spring is affixed to the elongated portion of the cannula body.

In additional aspects, the elongated portion of the cannula body includes a locking pin, and the sleeve includes a slot configured to selectively engage the locking pin. Distal movement of the sleeve relative to the elongated portion of the cannula body may cause the slot of the sleeve to disengage the locking pin. A radial position of a mid-portion of the spring relative to the longitudinal axis may be able to be adjusted when the slot of the sleeve and the locking pin of the elongated portion of the cannula body are disengaged.

In aspects, proximal movement of the sleeve relative to the elongated portion of the cannula body causes the slot of the sleeve to engage the locking pin. Engagement between the slot of the sleeve and the locking pin of the elongated portion of the cannula body may secure a radial position of a mid-portion of the spring relative to the longitudinal axis.

In aspects, the sheath is made from at least one of a transparent material or a translucent material.

In additional aspects, the spring is a constant force spring.

In aspects, the surgical access device also includes an anchor engaged with the elongated portion of the cannula body, and disposed proximally of the spring of the fixation mechanism. The anchor may be longitudinally translatable relative to the elongated portion of the cannula body.

The present disclosure also relates to a fixation mechanism for use with a surgical access device. The fixation mechanism includes a sleeve, a spring, and a sheath. The sleeve defines a longitudinal axis, and radially surrounding a portion of an elongated portion of the surgical access device. The sleeve is rotatable about the longitudinal axis relative to the elongated portion and is longitudinally translatable relative to the elongated portion. A proximal portion of the spring is affixed to the sleeve, and a distal portion of the spring is affixed to the elongated portion. The sheath radially surrounds the spring. Rotation of the sleeve about the longitudinal axis relative to the elongated portion causes the spring to move from a first position where a mid-portion of the spring is disposed a first distance from the elongated portion, to a second position where the mid-portion of the spring is disposed a second distance from the elongated portion, the second distance being greater than the first distance.

In aspects, the sheath radially surrounds a distal portion of the sleeve, and radially surrounds a distal portion of the elongated portion of the surgical access device.

In aspects, the spring is a constant force spring.

In additional aspects, the sleeve includes a slot configured to engage a locking pin of the elongated portion of the surgical access device to hinder rotation of the sleeve about the longitudinal axis relative to the elongated portion of the surgical access device.

BRIEF DESCRIPTION OF THE DRAWINGS

Various aspects of the present disclosure are illustrated herein with reference to the accompanying drawings, wherein.

DETAILED DESCRIPTION

Figure 1:
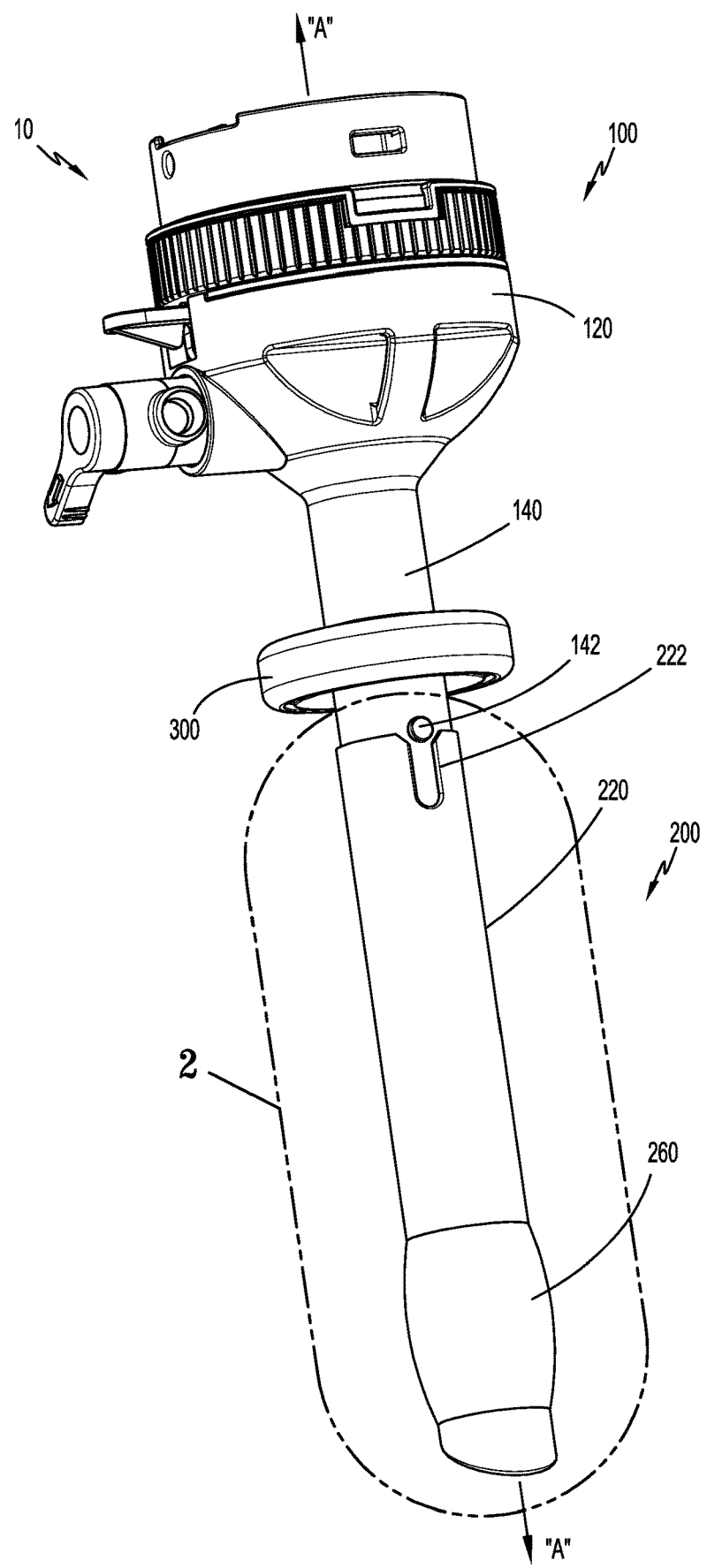
FIG. 1 is a perspective view of a surgical access device illustrating a fixation mechanism in an undeployed configuration.

Aspects of the presently disclosed surgical access device will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Generally, the surgical access device or cannula, often part of a trocar assembly, may be employed during surgery (e.g., laparoscopic surgery) and may, in various aspects, provide for the sealed access of laparoscopic surgical instruments into an insufflated body cavity, such as the abdominal cavity. The cannula is usable with an obturator insertable therethrough. The cannula and obturator are separate components but are capable of being selectively connected together. For example, the obturator may be inserted into and through the cannula until the handle of the obturator engages, e.g., selectively locks into, a proximal housing of the cannula. In this initial position, the trocar assembly is employed to tunnel through an anatomical structure, e.g., the abdominal wall, either by making a new passage through the structure or by passing through an existing opening through the structure. Once the trocar assembly has tunneled through the anatomical structure, the obturator is removed, leaving the cannula in place in the structure, e.g., in the incision created by the trocar assembly. The proximal housing of the cannula may include seals or valves that prevent the escape of insufflation gases from the body cavity, while also allowing surgical instruments to be inserted into the body cavity.

Additionally, the surgical access device of the present disclosure includes a fixation mechanism configured to engage tissue to help maintain the cannula in its position relative to the body during use.

FIGS. 1-5 illustrate an aspect of a surgical access device according to the present disclosure. With initial reference to FIG. 1, the surgical access device 10 includes a cannula body 100 and a fixation mechanism 200. The cannula body 100 includes a proximal housing 120 at its proximal end, and includes an elongated portion 140 extending distally from the proximal housing 120. The elongated portion 140 defines a channel 150 (FIG. 3) extending therethrough, and defines a longitudinal axis "A-A." An obturator (not shown) is insertable through the channel 150 and is engageable with the proximal housing 120, for instance.

Figure 2:
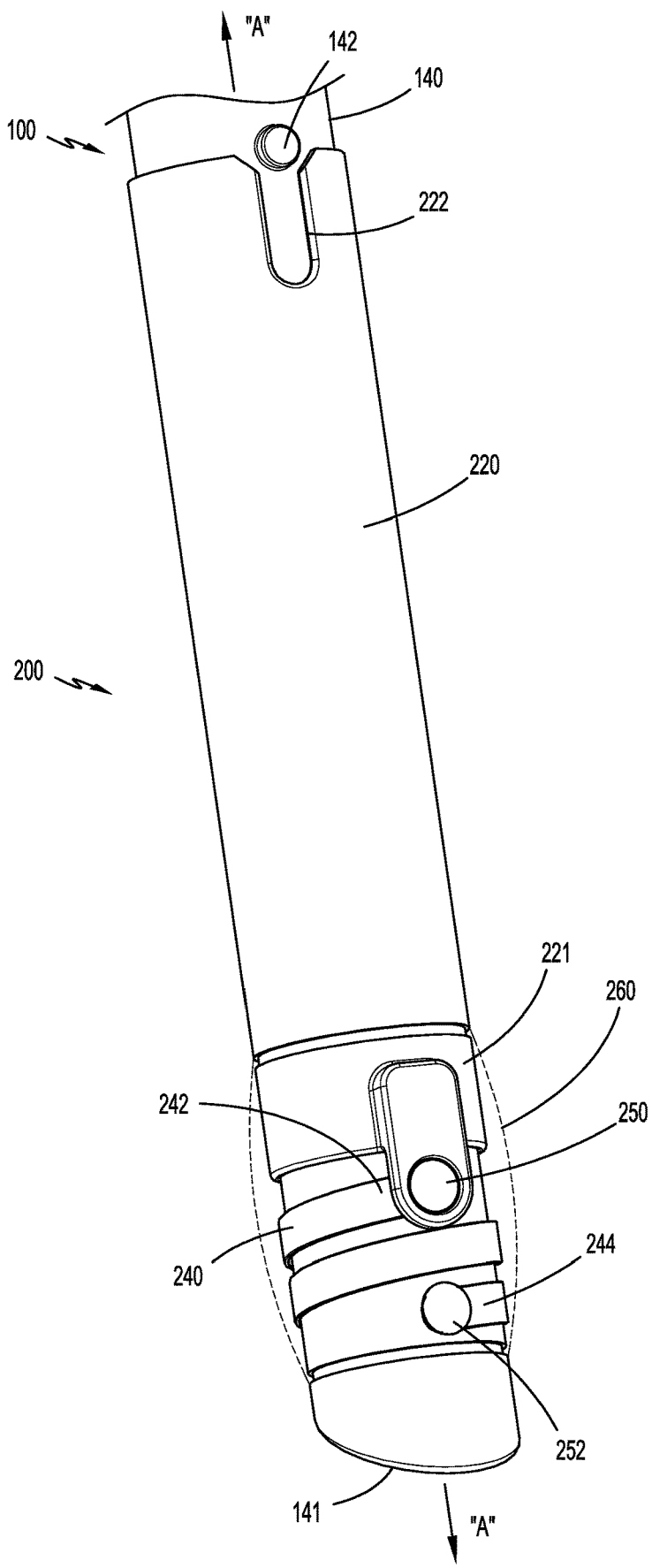
FIG. 2 is an enlarged view of the area of detail indicated in FIG. 1.

With particular reference to FIG. 2, the fixation mechanism 200 is disposed in mechanical cooperation with the elongated portion 140 of the cannula body 100, and includes a sleeve 220, a biasing element or spring 240, and a sheath 260. As discussed in detail below, the spring 240 is radially adjustable in response to rotation of the sleeve 220 (i.e., expansion or contraction).

Figure 3:
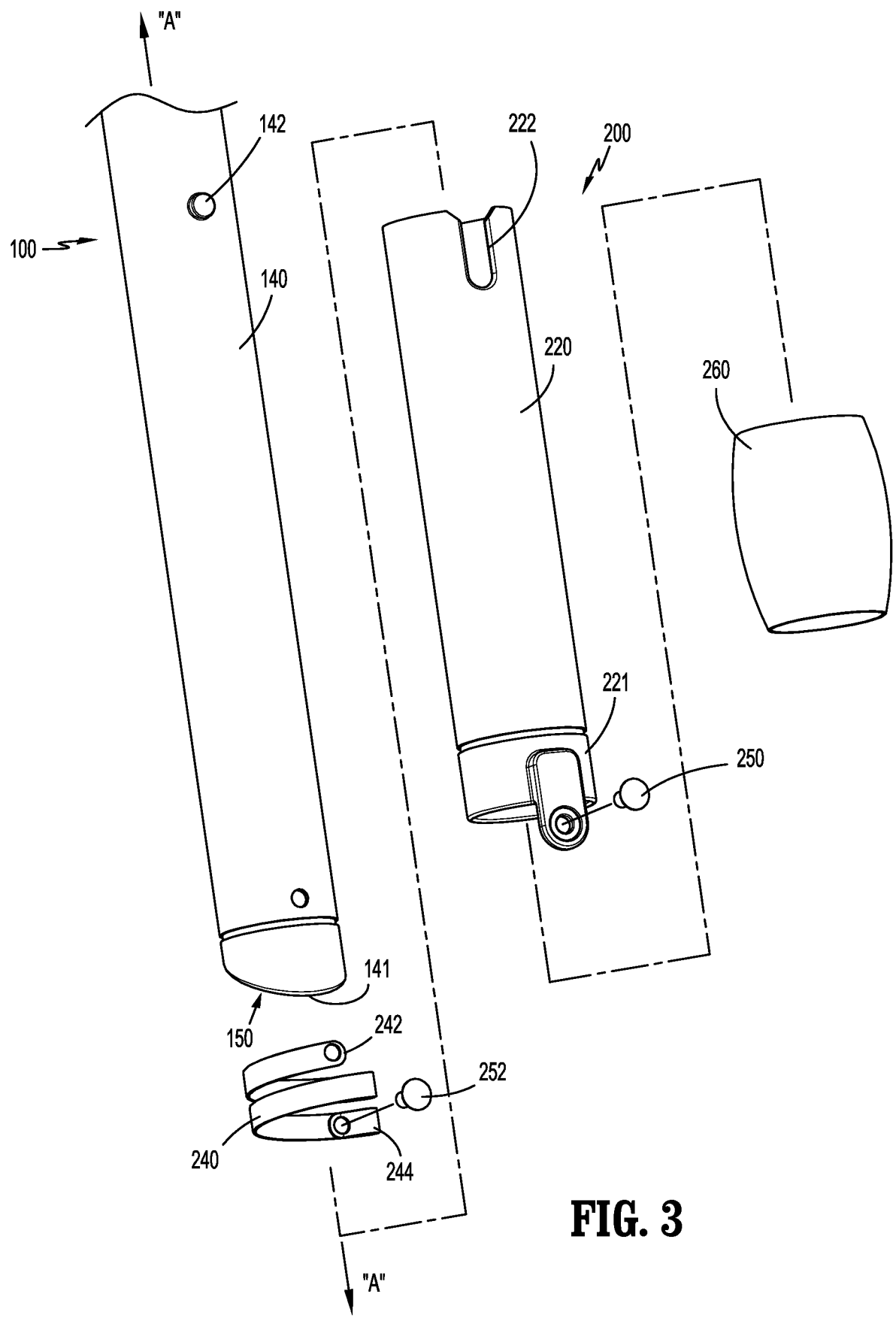
FIG. 3 is an assembly view of the surgical access device of FIG. 1.

Referring to FIGS. 1-3, the engagement between the fixation mechanism 200 and the cannula body 100 is shown. The sleeve 220 radially surrounds a portion of the elongated portion 140 of the cannula body 100, and is rotatable about the longitudinal axis "A-A" relative to the elongated portion 140. A first, proximal end 242 of the spring 240 is affixed to a distal portion of the sleeve 220 (e.g., with a first rivet 250), and a second, distal end 244 of the spring 240 is affixed to a portion of the elongated portion 140 of the cannula body 100 (e.g., with a second rivet 252). The sheath 260 radially surrounds the spring 240, a portion of the elongated portion 140, and a portion of the sleeve 220.

The sleeve 220 is rotatable about the longitudinal axis "A-A" relative to the elongated portion 140 of the cannula body 100. The sleeve 220 is also longitudinally translatable relative to the elongated portion 140 between a first, proximal position where a slot 222 of the sleeve 220 engages a locking pin 142 extending radially outward from the elongated portion 140 (FIG. 5), and a second, distal position where the slot 222 of the sleeve is disengaged from the locking pin 142 (FIGS. 1, 2 and 4).

More particularly, a predetermined amount of rotation of the sleeve 220 about the longitudinal axis "A-A" in a first direction (in the general direction of arrow "B" in FIG. 5) relative to the elongated portion 140 causes a portion (e.g., a mid-portion 246) of the spring 240 to move radially outward away from the longitudinal axis "A-A" (in the general direction of arrows "C" and "D" in FIG. 5) and an outer surface of the elongated portion 140, from the first position to the second position. Likewise, a predetermined amount of rotation of the sleeve 220 about the longitudinal axis "A-A" in a second direction (in the general opposite direction of arrow "B" in FIG. 5) relative to the elongated portion 140 causes the portion (e.g., the mid-portion 246) of the spring 240 to move radially inward toward the longitudinal axis "A-A" and the outer surface of the elongated portion 140 from the second position to the first position. In aspects, the spring 240 is a single constant force spring, which may enable or facilitate the radial expansion or outward movement of portions of the spring 240.

Figure 4:
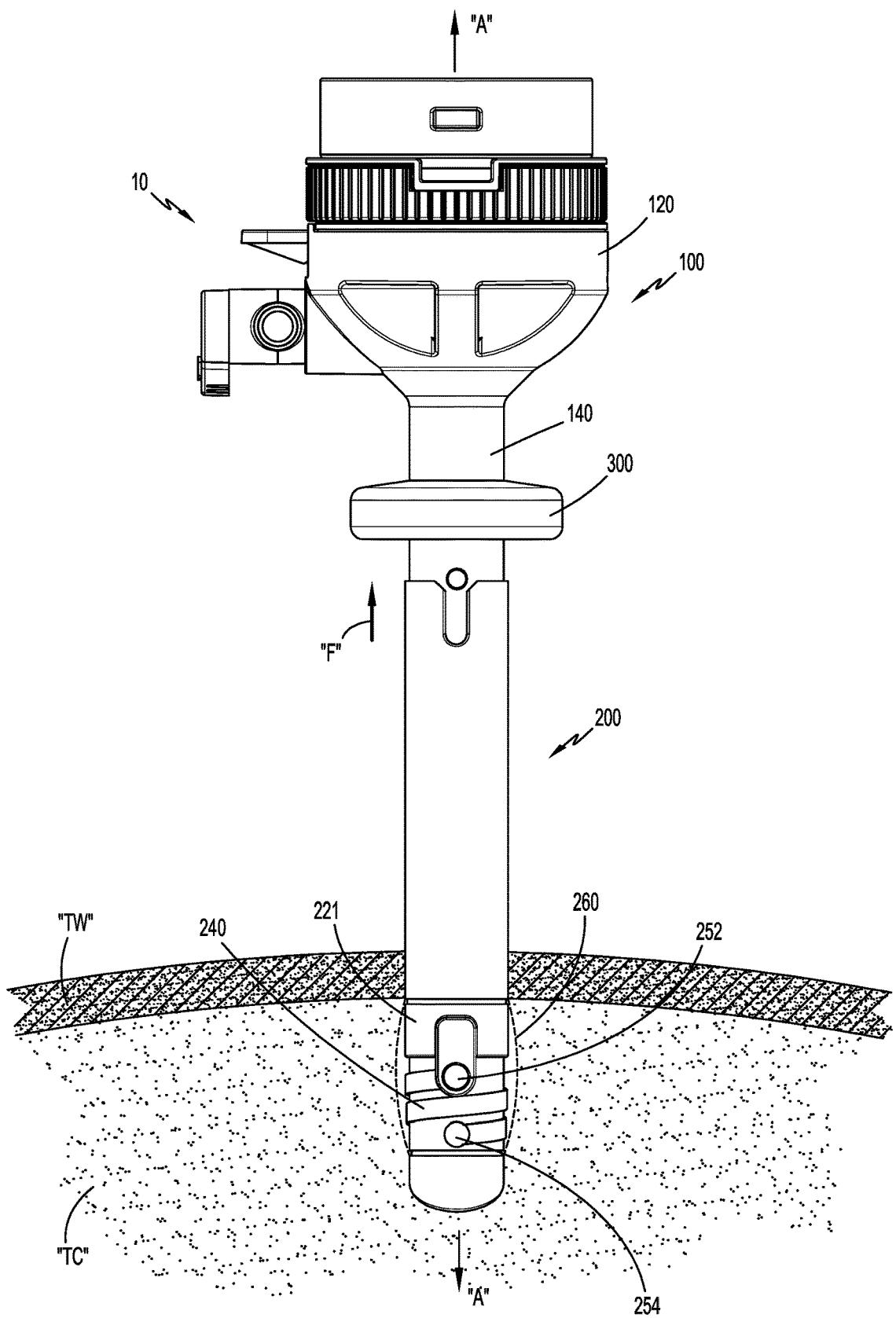
FIG. 4 is a side view of the surgical access device of FIGS. 1-3 within tissue illustrating the fixation mechanism in an undeployed configuration and an anchor in a proximal position.
Figure 5:
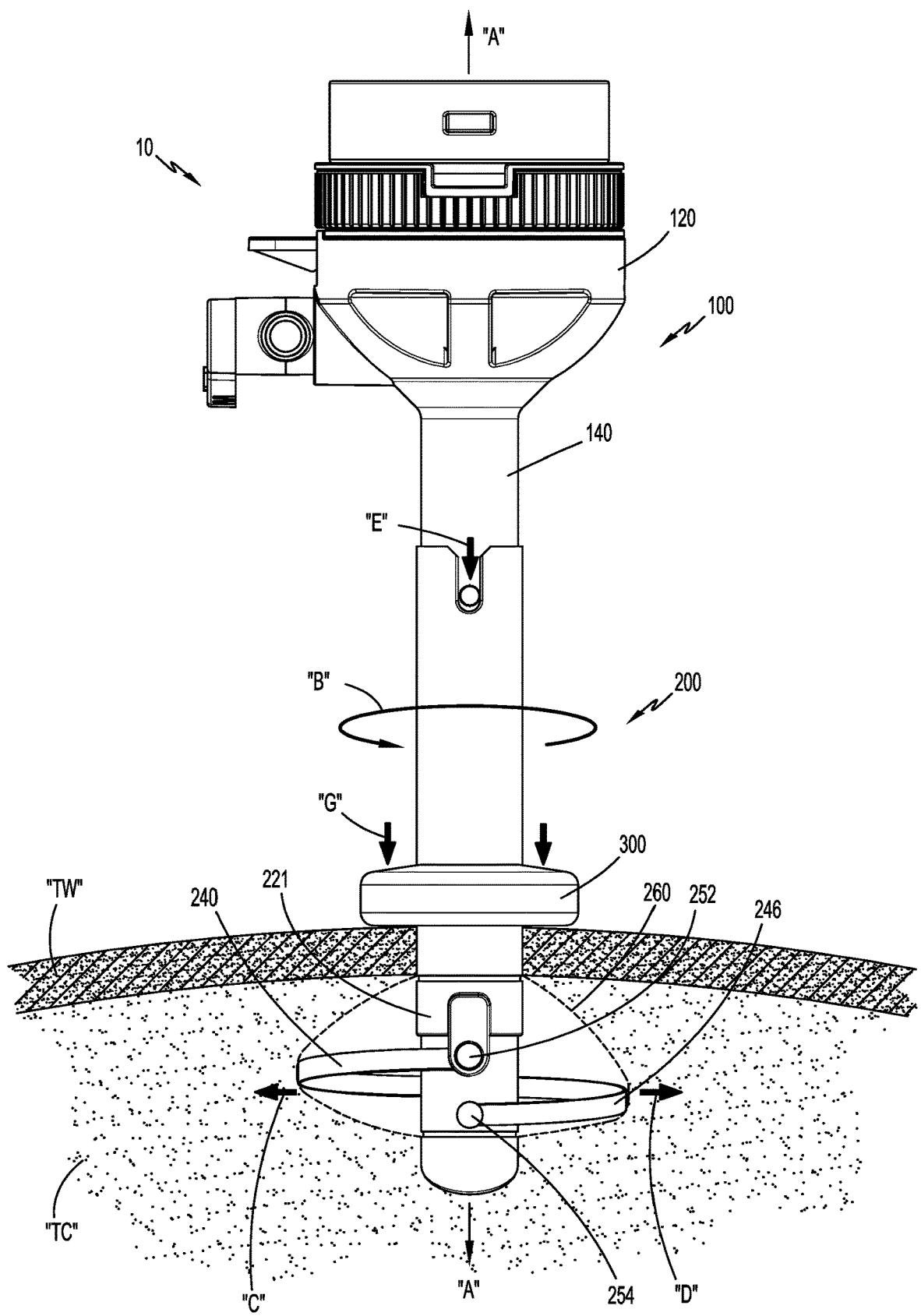
FIG. 5 is a side view of the surgical access device of FIGS. 1-4 within tissue illustrating the fixation mechanism in a deployed configuration and the anchor in a distal position.

Additionally, and with continued reference to FIGS. 4 and 5, distal movement of the sleeve 220 (in the general direction of arrow "E" in FIG. 5) relative to the elongated portion 140 of the cannula body 100 causes the slot 222 of the sleeve 220 to disengage from the locking pin 142. Further, when the slot 222 of the sleeve 220 is radially aligned with the locking pin 142, proximal movement of the sleeve 220 (in the general direction of arrow "F" in FIG. 4) relative to the elongated portion 140 of the cannula body causes the slot 222 of the sleeve 220 to engage the locking pin 142. When the slot 222 of the sleeve 220 is engaged with the locking pin 142 (FIG. 5), the sleeve 220 is restricted or prevented from rotating relative to the elongated portion 140 of the cannula body 100. When the slot 222 of the sleeve 220 is not engaged with the locking pin 142 (FIG. 4), the sleeve 220 is free to rotate relative to the elongated portion 140 of the cannula body 100. In various aspects, the sleeve 220 includes a gripping portion to facilitate rotating and translating the sleeve 220 relative to the elongated portion 140.

In various aspects, the elongated portion 140 includes a single locking pin 142. Here, one full rotation of the sleeve 220 relative to the elongated portion 140 of the cannula body 100 causes the spring 240 to transition between an undeployed or collapsed configuration (FIG. 4) and a deployed (or fully deployed) or expanded configuration (FIG. 5).

In various aspects, the elongated portion 140 of the cannula body 100 may include more than one locking pin 142 extending therefrom. The multiple locking pins 142 may be radially spaced from each other, and may correspond to various stages of radial expansion of the spring 240, for instance. In such aspects, the sleeve 220 may include the same number of slots 222 as there are locking pins 142.

With particular reference to FIG. 2, the sheath 260 is affixed to and radially surrounds a distal portion of the sleeve 220, and a distal portion of the elongated portion 140 of the cannula body 100. Additionally, the sheath 260 radially surrounds the spring 240. The sheath 260 is configured to constrain the spring 240, protect the spring 240, and protect tissue from direct contact with the spring 240. In aspects, the sheath 260 is made from a transparent or translucent material, such as a plastic film or elastomer, which may facilitate a visual inspection of the sleeve 220 and/or the spring 240, for instance.

Referring now to FIGS. 1, 4 and 5, an anchor 300 is shown. The anchor 300 is positionable around the cannula body 100 such that the anchor 300 radially surrounds a portion of the elongated portion 140. More particularly, the anchor 300 is longitudinally translatable (in the general direction of arrow "G" in FIG. 5, and in the opposite direction) along the elongated portion 140 between a first position, where the anchor 300 is farther away from the distal end 141 of the elongated portion 140 (FIG. 4), and a second position, wherein the anchor 300 is closer to the distal end 141 of the elongated portion 140 (FIG. 5). The anchor 300 may have a frictional engagement with the elongated portion 140 such that the anchor 300 can be pushed/pulled to move between its first and second positions.

In various aspects, the anchor 300 may be positioned around the sleeve 220 of the fixation mechanism 200. Here, the anchor 300 is longitudinally translatable along the sleeve 220 between a first position, where the anchor 300 is farther away from a distal end 221 of the sleeve 220 (and distally of the slot 222 of the sleeve 220, for instance), and a second position, wherein the anchor 300 is closer to the distal end 221 of the sleeve 220.

In use, the distal end 141 of the elongated portion 140 of the cannula body 100 is inserted into a tissue cavity "TC" while the fixation mechanism 200 is in its undeployed configuration (FIG. 4), which corresponds to the spring 240 being in a radially contracted position. Next, to move the fixation mechanism 200 to its deployed configuration, which corresponds to the spring 240 being in a radially expanded position, the user initially pushes or translates the sleeve 220 distally relative to the elongated portion 140 in the general direction of arrow "E" (FIG. 5) to cause the slot 222 of the sleeve 200 to disengage from the locking pin 142 of the elongated portion 140. Once the slot 222 is disengaged from the locking pin 142 (FIG. 4), the user is able to rotate the sleeve 220 relative to the elongated portion 140 (e.g., in the general direction of arrow "B" in FIG. 5). As discussed above, this rotation of the sleeve 220 causes the spring 240 (or the mid-portion 246 thereof) to radially expand into its second position (FIG. 5). Next, to lock the spring 240 in its second, radially-expanded position, the sleeve 220 is moved proximally such that the slot 222 engages the locking pin 142 of the elongated portion 140. As noted above, the elongated portion 142 may have a single locking pin 142 or multiple locking pins 142, which correspond to various degrees of radial expansion of the spring 240, for instance. Additionally, prior to moving the sleeve 220 proximally, the sleeve 220 may have to be rotated (in either the general direction of arrow "B" (FIG. 5) or in the opposite direction) to align the slot 222 with the locking pin 142.

As shown in FIG. 5, when the spring 240 is in the second position, the fixation mechanism 200 is within the tissue cavity "C" and is adjacent a distal portion of a tissue wall "TW," thereby resisting a proximally-directed force acting on the surgical access device 10.

Next, the anchor 300 can be moved distally from its first, proximal position (FIG. 4) to its second, distal position (FIG. 5) such that the anchor 300 contacts a proximal portion of the tissue wall "TW," thereby sandwiching the tissue wall "TW" between the anchor 300 and the fixation mechanism 200, and fixing the longitudinal position of the cannula body 100 relative to the tissue wall "TW."

To remove the surgical access device 10 from contact with tissue, the anchor 300 is moved proximally, the sleeve 220 is moved distally relative to the elongated portion 140 to disengage the slot 222 from the locking pin 142, the sleeve 220 is rotated in the opposite direction of arrow "B" (FIG. 5) relative to the elongated portion 140 to cause the fixation mechanism 200 to move to its first configuration, the sleeve 220 may then be moved proximally relative to the elongated portion 140 to cause the slot 222 to engage the locking pin 142, and then the distal portion of the surgical access device 10 is removed through the incision in the tissue wall "TW."

The present disclosure also relates to a method of deploying the fixation mechanism 200 of a surgical access device 10. The method includes translating the sleeve 220 distally relative to the elongated portion 140 to disengage the slot 222 from the locking pin 142, rotating the sleeve 220 in a first direction about the longitudinal axis "A-A" relative to the elongated portion 140 to radially expand the spring 240 of the fixation mechanism 200, translating the sleeve 220 proximally relative to the elongated portion 140 to engage the slot 222 with the locking pin 142 to prevent rotation therebetween, translating the sleeve 220 distally relative to the elongated portion 140 to disengage the slot 222 from the locking pin 142, rotating the sleeve 220 in a second direction about the longitudinal axis "A-A" relative to the elongated portion 140 to radially contract the spring 240 of the fixation mechanism 200, and translating the sleeve 220 proximally relative to the elongated portion 140 to engage the slot 222 with the locking pin 142 to prevent rotation therebetween.

While the above description contains many specifics, these specifics should not be construed as limitations on the scope of the present disclosure, but merely as illustrations of various aspects thereof. Therefore, the above description should not be construed as limiting, but merely as exemplifications of various aspects. Those skilled in the art will envision other modifications within the scope and spirit of the claims appended hereto.

What is claimed is:
1. A fixation mechanism for use with a surgical access device, the fixation mechanism comprising:
 a sleeve defining a longitudinal axis, the sleeve configured to radially surround a portion of an elongated portion of the surgical access device, the sleeve rotatable about the longitudinal axis relative to the elongated portion and axially translatable relative to the elongated portion;

a spring, a portion of the spring affixed to the sleeve; and a sheath radially surrounding at least a portion of the spring, wherein rotation of the sleeve about the longitudinal axis relative to the elongated portion causes the spring to move from a first position where a mid-portion of the spring is disposed a first distance from the longitudinal axis, to a second position where the mid-portion of the spring is disposed a second distance from the longitudinal axis, the second distance is greater than the first distance.

2. The fixation mechanism according to claim 1, wherein the sheath radially surrounds a distal portion of the sleeve.

3. The fixation mechanism according to claim 1, wherein the sheath radially surrounds a proximal portion of the spring.

4. The fixation mechanism according to claim 1, wherein the sheath radially surrounds a distal portion of the spring.

5. The fixation mechanism according to claim 1, wherein the sheath radially surrounds an entirety of the spring.

6. The fixation mechanism according to claim 1, wherein the spring is a constant force spring.

7. The fixation mechanism according to claim 1, wherein the sleeve includes a slot configured to engage a pin on the elongated portion to hinder rotation of the sleeve about the longitudinal axis relative to the elongated portion.

8. The fixation mechanism according to claim 7, wherein distal movement of the sleeve relative to the elongated portion defines a gap between the slot and the pin.

9. The fixation mechanism according to claim 7, wherein a radial position of a mid-portion of the spring relative to the longitudinal axis is adjustable when the slot is spaced apart from the pin.

10. The fixation mechanism according to claim 1, wherein a radial position of a mid-portion of the spring relative to the longitudinal axis is adjustable.

11. The fixation mechanism according to claim 1, wherein a proximal portion of the spring is affixed to the sleeve.

12. A fixation mechanism for use with a surgical access device, the fixation mechanism comprising:
    a sleeve defining a longitudinal axis, the sleeve configured to radially surround a portion of an elongated portion of the surgical access device, the sleeve rotatable about the longitudinal axis relative to the elongated portion and axially translatable relative to the elongated portion, the sleeve including a slot configured to selectively engage a pin of the elongated portion; and
    a spring, a first portion of the spring engaged with the sleeve and a second portion of the spring engaged with a distal portion of the elongated portion,
    wherein rotation of the sleeve about the longitudinal axis relative to the elongated portion causes a portion of the spring to move away from the longitudinal axis.

13. The fixation mechanism according to claim 12, wherein the first portion of the spring is a proximal portion of the spring, and the second portion of the spring is a distal portion of the spring.

14. The fixation mechanism according to claim 12, further including a sheath radially surrounding at least a portion of the spring.

15. The fixation mechanism according to claim 14, wherein the sheath radially surrounds a distal portion of the sleeve.

16. The fixation mechanism according to claim 14, wherein the sheath radially surrounds an entirety of the spring.

17. The fixation mechanism according to claim 12, wherein a proximal portion of the spring is affixed to the sleeve.

18. The fixation mechanism according to claim 12, wherein distal movement of the sleeve relative to the elongated portion defines a gap between the slot and the pin.

19. The fixation mechanism according to claim 18, wherein proximal movement of the sleeve relative to the elongated portion causes the slot to engage the pin.

20. The fixation mechanism according to claim 12, wherein a radial position of a mid-portion of the spring relative to the longitudinal axis is adjustable.

* * * * *